(12) United States Patent
Anderson et al.

(10) Patent No.: US 7,031,768 B2
(45) Date of Patent: Apr. 18, 2006

(54) CONTROLLED DOSAGE DRUG DELIVERY

(75) Inventors: Carter R. Anderson, Inver Grove Heights, MN (US); Clayton J. Anderson, Burnsville, MN (US); Walter L. Sembrowich, North Oaks, MN (US); Russell L. Morris, Lindstrom, MN (US)

(73) Assignee: Birch Point Medical, Inc., Oakdale, MN (US)

( * ) Notice: Subject to any disclaimer, the term of this patent is extended or adjusted under 35 U.S.C. 154(b) by 691 days.

(21) Appl. No.: 10/166,157

(22) Filed: Jun. 10, 2002

(65) Prior Publication Data
US 2003/0028170 A1 Feb. 6, 2003

Related U.S. Application Data

(63) Continuation-in-part of application No. 09/674,211, filed on Dec. 18, 2000, now abandoned.

(60) Provisional application No. 60/098,652, filed on Aug. 31, 1998.

(51) Int. Cl.
A61N 1/30 (2006.01)

(52) U.S. Cl. ...................................... 604/20
(58) Field of Classification Search ............ 607/2; 604/20
See application file for complete search history.

(56) References Cited

U.S. PATENT DOCUMENTS

| 116,562 A | 7/1871 | Collins |
|---|---|---|
| 175,974 A | 4/1876 | Hall |
| 222,276 A | 12/1879 | Hunter |
| 385,556 A | 7/1888 | Hoke |
| 393,741 A | 12/1888 | Collins |
| 770,014 A | 9/1904 | Linn |
| 857,664 A | 6/1907 | Overman |
| 1,967,927 A | 7/1934 | Deutsch |
| 4,619,252 A | 10/1986 | Ibbott |
| 4,713,050 A | 12/1987 | Sibalis |
| 4,722,726 A | 2/1988 | Sanderson et al. |
| 4,747,819 A | 5/1988 | Phipps et al. |
| 4,752,285 A | 6/1988 | Petelenz et al. |
| 4,767,401 A | 8/1988 | Seiderman |
| 4,927,408 A | 5/1990 | Haak et al. |
| 4,950,229 A | 8/1990 | Sage, Jr. |
| 5,160,315 A | 11/1992 | Heinecke et al. |

(Continued)

FOREIGN PATENT DOCUMENTS

DE 1967927 7/1934

(Continued)

OTHER PUBLICATIONS

Aiontophoresis: Applications in Transdermal Medication Delivery@, Charles T. Costello, Arthur H. Jeske, *Physical Therapy*, vol. 75, No. 6, Jun. 1995, pp. 554-563.

(Continued)

*Primary Examiner*—Mark Bockelman
(74) *Attorney, Agent, or Firm*—Nikolai & Mersereau, P.A.; C. G. Mersereau

(57) ABSTRACT

A planar disposable transdermal iontophoretic delivery system is disclosed which includes amounts of an oxidizable species and a reducible species connected by a common conductor forming a galvanic battery for serving as the sole source of power and control for the system, an amount of a therapeutic agent is provided to be driven through the skin of a patient solely through the use of the galvanic battery. The galvanic battery is provided with a lot-tested coulombic capacity rating to predict dosage.

36 Claims, 11 Drawing Sheets

U.S. PATENT DOCUMENTS

| | | |
|---|---|---|
| 5,162,042 A | 11/1992 | Gyory et al. |
| 5,203,768 A | 4/1993 | Haak et al. |
| 5,221,254 A | 6/1993 | Phipps |
| 5,254,081 A | 10/1993 | Maurer et al. |
| 5,295,979 A | 3/1994 | DeLaurentis et al. |
| 5,298,017 A | 3/1994 | Theeuwes et al. |
| 5,320,731 A | 6/1994 | Muller et al. |
| 5,322,520 A | 6/1994 | Milder |
| 5,354,321 A | 10/1994 | Berger |
| 5,356,632 A | 10/1994 | Gross et al. |
| 5,358,483 A | 10/1994 | Sibalis |
| 5,403,275 A | 4/1995 | Phipps |
| 5,405,317 A | 4/1995 | Myers et al. |
| 5,431,625 A | 7/1995 | Fabian et al. |
| 5,436,090 A * | 7/1995 | Kono et al. .......... 429/317 |
| 5,458,569 A | 10/1995 | Kirk, III et al. |
| 5,466,217 A | 11/1995 | Myers et al. |
| 5,533,971 A | 7/1996 | Phipps |
| 5,605,536 A | 2/1997 | Sibalis |
| 5,624,415 A | 4/1997 | Cormier et al. |
| 5,651,768 A | 7/1997 | Sibalis |
| 5,685,837 A | 11/1997 | Horstmann |
| 5,759,564 A | 6/1998 | Milder et al. |
| 5,772,688 A | 6/1998 | Muroki |
| 5,983,130 A | 11/1999 | Phipps et al. |

FOREIGN PATENT DOCUMENTS

| | | |
|---|---|---|
| DE | 2263792 | 3/1974 |
| EP | 0060451 | 3/1982 |
| EP | 0308572 | 8/1984 |
| EP | 456 122 | 5/1991 |
| EP | 0 893 139 | 7/1998 |
| FR | 2 263 792 A | 10/1975 |
| GB | 410009 | 5/1934 |
| GB | 2.206493 | 1/1989 |
| GB | 0456122 | 11/1995 |
| WO | WO 01/49365 | 7/2001 |

OTHER PUBLICATIONS

Atransdermal Iontophoresis. Part I: Basic Principles and Considerations@, Vinod Nair, Omathanu Pillai, Ramarao Poduri and Ramesh Panchagnula, *Methods Find Exp Clin Pharmacol*, 1999, 21(2): 139-151.

* cited by examiner

CONTROLLED DOSAGE DRUG DELIVERY

This application is a Continuation-In-Part of application Ser. No. 09/674,211, filed Dec. 18, 2000, now abandoned, which is incorporated by reference herein in its entirety and itself is a complete application claiming priority based on Provisional Application No. 60/098,652, filed Aug. 31, 1998.

BACKGROUND OF THE INVENTION

I. Field of the Invention

The present invention deals generally with transdermal delivery of therapeutic agents by use of an applied electromotive force (emf), commonly known as iontophoresis. More particularly, the invention is directed to a system for iontophoresis that is self-contained, and quantitatively self-limiting. The system is contained preferably in a rather small skin-worn patch which contains electrodes and a therapeutic agent. When applied to the skin, the system completes a circuit and spontaneously initiates the flow of a galvanic current of measured, limited duration corresponding to the amount of therapeutic agent delivered. The system may be anode or cathode limited. The power source/dosage control systems are based on a galvanic couple power source selected from manufactured lots or batches of such power sources or source components of tested capacity so that each system capacity can also be designated on labels with a high degree of confidence. The system is self contained.

II. Related Art

The process of iontophoresis was described by LeDuc in 1908, and has since found commercial use in the delivery of ionically charged compounds such as pilocarpine, dexamethasone, and lidocaine. In this delivery method, ions bearing a positive charge are driven across the skin at the site of an electrolytic electrical system anode, while ions bearing a negative charge are driven across the skin at the site of an electrolytic electrical system cathode.

With iontophoretic devices, the application time and level of current flow (usually reported in units of milli-amp minutes) between the anode and cathode is directly correlated to the amount of drug delivered. The efficiency of drug delivery in an iontophoretic system can be measured by the proportion of current carried by the drug molecule, relative to the current carried by competing non-medication ions having the same charge as the medication.

At present, iontophoresis devices conventionally include two electrodes attached to a patient, each connected via a wire to a microprocessor-controlled electrical instrument. An illustration of a conventional iontophoretic system is shown in FIG. 1. Medication is placed under one or both of the electrodes for delivery into the body as the instrument is activated. The instrument is designed to regulate current flow and application time. Examples of such instruments are described in U.S. Pat. Nos. 5,254,081 and 5,431,625. Power for these devices is usually provided by DC batteries, which when providing power for the microprocessor-controlled circuitry allow application of a voltage to the electrodes to create a regulated current flow. The automated control of current flow and time (milliamp-minutes) is of great advantage in order to prevent excessive dosages of therapeutic agents from being delivered. However, these battery powered microprocessor-controlled systems are disadvantaged by the fact that patients are attached by wire to an instrument which limits patient mobility and ability to conduct normal daily activities. A typical application period is approximately 20 minutes to 2 hours, which consumes instrument, caregiver and patient time.

Such an early system is illustrated schematically in FIG. 1 which includes an instrument case 10 for containing a battery-powered current source, a microprocessor-controller, all necessary electronic circuitry and other controls (not shown). An output display is shown at 12. Positive and negative terminals 14 and 16 are connected respectively to external electrode systems 18 and 20 designed to be attached to the patient. Electrode 18 contains a buffer or salt solution at 22 and the electrode 20 is the working electrode containing the medication or therapeutic agent chamber at 24. At all times the patient must remain connected to the device 10 via electrode-connecting wires 26 and 28. All other necessary electronic circuitry for microprocessor-controlled current flow is contained in the instrument case 10.

More recently, wearable iontophoretic systems have been developed in which the electrical circuitry and power supplied are integrated into a single patch. These systems are advantageous in that they do not have external wires, and they are much smaller in size. Examples of such systems can be found in U.S. Pat. Nos. 5,358,483; 5,458,569; 5,466,217; 5,533,971; 5,605,536; and 5,651,768. However, these systems also have the drawback that they are relatively inflexible and expensive, owing to the multiple electronic components, battery power supplies and electrical interconnects.

U.S. Pat. No. 5,685,837 to Horstmann describes a wearable iontophoretic system, which can be designed to modulate current flow without use of microprocessor control In this design, each electrode consists of multi-layer sheet-like galvanic elements. Each sheet-like element incorporates a sandwiched electrolyte layer that collects oxidative and reductive byproducts. This does allow current flow to be regulated, e.g. gradually diminished, owing to the incorporation of very thin layers. The gradual current reduction follows a Nernstian defined voltage reduction from collection of byproducts in the electrolyte layer. The '837 invention is disadvantaged by 1) the need for a multi-layer electrode construction that can be challenging to manufacture and 2) a gradual, e.g. protracted, decrease in current where a more constant delivery rate, followed by an abrupt completion, would be desired.

Power to drive iontophoretic current flow can also be supplied by galvanic means, which utilizes dissimilar anode and cathode materials to produce a spontaneous current flow when they are contacted with the body. These systems hold the advantage that separate electrical circuitry and battery sources are not required. An iontophoretic device, not of the transdermal type, but one which utilizes galvanic means is described in U.S. Pat. No. 5,322,520. That system involves the use of two dissimilar galvanic materials in an implanted device or catheter system designed to deliver oligodynamic metal ions from its surface in order to kill bacteria on or near it. Yet another system for a urinary catheter is shown by DeLaurentis et al, in U.S. Pat. No. 5,295,979. These devices are disadvantaged by the fact that the amount of medication (active species) delivered is not automatically regulated and they require a timely removal of the device from the body to prevent a potentially toxic over-dosage of medication or excessive electrode by-product from being released. Still other galvanic battery patent examples are found in U.S. Pat. No. 5,162,042; UK 2,206,493; and UK 410,009.

A device disclosed by Muller et al in U.S. Pat. No. 5,320,731 uses an electrode consuming technique as a means to regulate dosage without the need to incorporate a microprocessor. In the '731 system, electrodes are described which are consumed as current flows and are designed in a manner where consumption of the electrode is complete at the desired delivery dosage. However, this invention requires an external connected power source and means to monitor voltage, therefore advantage is limited.

Additionally, while prior art galvanic devices may have a "maximum" delivery capacity as defined by an amount of active materials incorporated within, the "actual" delivered capacities will vary (and in fact therefore be "unknown") owing, for example, to unpredictable breaks in electrical contact prior to full consumption of active materials, and/or corrosive side reactions which will consume active material without providing iontophoretic current. Other reasons for inaccuracies in predictability appear below.

From the above, it will be appreciated that a simplified skin-patch-type system for iontophoresis that is self-contained, inexpensive and relatively simple with respect to electrical aspects, particularly one which further controls the amount of therapeutic agent to be delivered would be in great demand.

Accordingly, an advantage of the present invention is the provision of a self-contained, self-limiting transdermal iontophoretic drug delivery device. The present invention provides such a device which is galvanically powered and does not require any separate current source or electric circuitry including an embodiment in the form of a thin planar, conforming, and relatively small iontophoretic wearable skin patch-type device which does not interfere with the daily activities of the wearer.

The present invention provides a wearable galvanic iontophoresing device that is designed to deliver a controlled dosage of medication in an automated fashion, based on a more reliable, test-verified galvanic charge capacity in the corresponding power source. Provision can be made to eliminate oxygen reduction current and associated pH change in the system. Both techniques act to prevent an over-dosage of medication or excessive release of electrode by-product materials.

A method for delivering a controlled dosage at a controlled rate of medication iontophoretically in an automated fashion entirely dependent on a self-contained skin-patch device is also provided.

Other advantages of the invention will become apparent to those skilled in the art upon further familiarization with the specification, drawings and claims herein.

SUMMARY OF THE INVENTION

The present invention provides advances in benign transdermal drug delivery. The invention provides a self-regulating, wearable iontophoretic system for the transdermal delivery of a therapeutic agent that automatically and inherently provides a controlled or limited amount and controls the rate of delivery. The wearable iontophoretic system is preferably in the form of an adhesively applied skin patch which may include a self-sticking hypoallergenic adhesive layer or be taped in place.

The iontophoretic patch of the invention basically includes two chambers; namely, a cationic drug chamber and an anionic drug chamber. The cationic drug chamber contains an electrode which includes material or coating of an electrochemically oxidizable species. The anionic drug chamber contains an electrode which likewise includes an electrochemically reducible species. The chambers are separated by a known distance and are electrically connected by a conductor.

Any suitable redox couple can be used as a battery. The oxidizable species and the reducible species preferably are selected so as to provide the desired spontaneous galvanic potential when the iontophoretic patch in which they are contained is in contact with a patient's body. By adjusting potential and conductor capacity, the rate of delivery can be adjusted and by adjusting (limiting) the amount of the oxidizable and/or reducible species, the amount of the dosage can be regulated.

With respect to dosage regulation an important aspect of the invention that enables high dosage rating accuracy for the iontophoretic patch devices is that the manufacturing process includes characterizing the charge capacity of batches or lots of the galvanic power sources or components (half-couples) in accordance with actual manufactured capacity rather than a target capacity. The capacity of the typical corresponding couple can be predicted with a greater degree of accuracy and any iontophoresis patch using one or more of these characterized galvanic power sources will also have (within close tolerances) a known capacity such that it may be designated or labeled as such with a high degree of confidence.

Thus, a lot or batch as per the Examples I–III, below, could be labeled in accordance with the test results as 80 mA-minutes ±10% per the inspection and testing procedure used in the examples. An untested lot with a target capacity of 80 A-minutes may in fact be well outside those characterization limits. This added confidence enables the galvanic power source not only to be the sole power source for the iontophoresis patch, but also to provide the only dosage control for that patch.

The exemplary embodiments of the iontophoretic wearable patch of the invention further include an impervious backing or top layer which holds the electrodes in place and carries a cell wall defining layer which has two separated openings to define anode and cathode cell cavities. Fluid is retained in the cavities by the presence of a hydrophilic absorbent layer which, in turn, may be held in place by a current distribution layer permeable to the passage of drug molecules. The patch may further or alternatively have a hypoallergenic adhesive layer also permeable to the passage of drug molecules on the bottom to attach to the skin or be attached utilizing an overlaying bandage material. A manual switch or current interrupting device may be provided for use by the patient to interrupt administration of the drug if desired. If desired, an opening may be provided to serve as an inlet for drug-containing fluids which may be injected into the delivery cells just prior to use. As used herein, the term "drug" refers to any therapeutic agent susceptible to transdermal delivery in accordance with the principles described herein.

The backing material may be high density polyethylene tape such as 3M No. 1523 or other occlusive material and the backing material defining the cell walls may be of polyethylene closed cell foam exemplified by 3M No. 1772 or similar material. The hydrophilic absorbent layer may include a material which forms a hydrophilic gel when contacted with aqueous solution such as polyacrylamide, or be made from cotton, gauze or other hydrophilic material. Porous membrane material such as nylon, polycarbonate, ethylene vinyl acetate (EVA) and cellulose acetate are examples of suitable materials for use as current distribution layer materials.

When the system is placed in contact with normal skin, an electric circuit is completed which allows passage of current and with it the delivery of drug compounds. As indicated, the rate of delivery may be controlled by the electromotive character of the particular electrode materials chosen, and the capacity of the conductor therebetween and the dosage controlled by use of a limited known amount of oxidizable and/or reducible material in the system as the depletion of either will extinguish the galvanic current and so the flow of therapeutic agent.

Accordingly, an important aspect of the present invention involves the preparation of the iontophoretic electrodes as a known, limiting amount of electro-active species must be associated with either the anode electrode, the cathode electrode or both. In this regard, for example, oxidizable wire or foil material of known weight and purity can be used; or an oxidizable coating of known amount can be deposited on the surface of an electrically conductive substrate. In this manner, a known amount of desired metal can be deposited over a wire or printed circuit substrate to produce an electrode with an oxidizable species of known content. In this regard, any known deposition process involving a particular metal could be used including dipping, electrolytic or electroplating, sputtering, etc. Likewise, a reducible coating of known amount may be deposited on the surface of the other end of the conductor using any known process in preparation of the anionic drug chamber electrode.

One example of a preferred approach to the preparation of the iontophoretic electrodes of the invention is to dip one end of a silver wire into molten zinc or magnesium and electrolytically generating a known amount of silver chloride on the other end of the wire. Untreated silver wire in the center serves to electrically connect the two electrodes. This process yields a controlled dosage galvanic battery which is thereafter assembled into the iontophoretic patch of the invention.

As will be explained, because of vagaries in manufacturing processes, which are characteristic of the production of large or even small batch (or lot) quantities of galvanic power cells or half-cells for power supplies, it has been found that manufacturing such cells to a particular target capacity using known quantities of materials does not alone produce the most accurate results insofar as labeling dosages for patches or other devices using the cells with a high degree of confidence is concerned.

Closer tolerances can be achieved by testing the capacity of an adequate sample of power sources (cells) or component (half-cells) from each batch or lot. Test results enable more accurate characterization of the actual charge capacity of the cells produced in that batch or lot which, in turn, enables designating or labeling the dosage of a corresponding iontophoresis device with greater confidence.

In addition, the materials of construction may be important to final capacity. Additional current associated with oxygen reduction can occur in cells after exhaustion of what was believed to be the controlling half-cell material. This further passage of current produces a device of higher than intended capacity. The phenomenon additionally, undesirably alters the pH of the drug solution. Where this may be a problem, another aspect of the invention also recognizes and solves this problem by (1) preferably limiting the oxidizable species in relation to the reducible species and (2) using a connecting conductor material where the residual material left exposed after consumption of the oxidative species in the cationic drug chamber corresponds to the reduction product (or byproduct) of the reducible species in the anionic chamber to produce a net zero voltage state after oxidizable species depletion.

According to the method of the invention, the technique includes the ability to produce patch devices or other embodiments to deliver (within limits such as ±10%) deliver any designated dosage of a therapeutic agent transdermally to a desired location using a self-contained wearable patch. According to the method and the construction of the patch, the therapeutic agent may be added at the time of manufacture as by incorporation into the hydrophilic absorbent layers of the drug chambers or may be added by injection into the chambers at the time of use. Of course, where medication is pre-packaged in the device, user convenience is improved by eliminating the necessity for the medication adding step. This may be overshadowed by the ease of packaging and storing dry patches which have a much greater shelf life.

BRIEF DESCRIPTION OF THE DRAWINGS

In the drawings, wherein like numerals are utilized to designate like parts throughout the same.

DETAILED DESCRIPTION

The detailed description of the present invention illustrates the principles of an advanced transdermal drug delivery system. The embodiments are described by using a very limited number of example configurations and material compositions, including therapeutic agents delivered. It is believed that the application of the principles encompassed by the present inventive concept, however, are much broader and, in reality, a great number of conductors, galvanic couples (oxidizable and reducible species), therapeutic agents to be delivered and actual configurations of the wearable patch are possible. Accordingly, the descriptions and accounts given herein are intended as examples and not meant to limit the scope of the invention in any manner.

Figure 1:
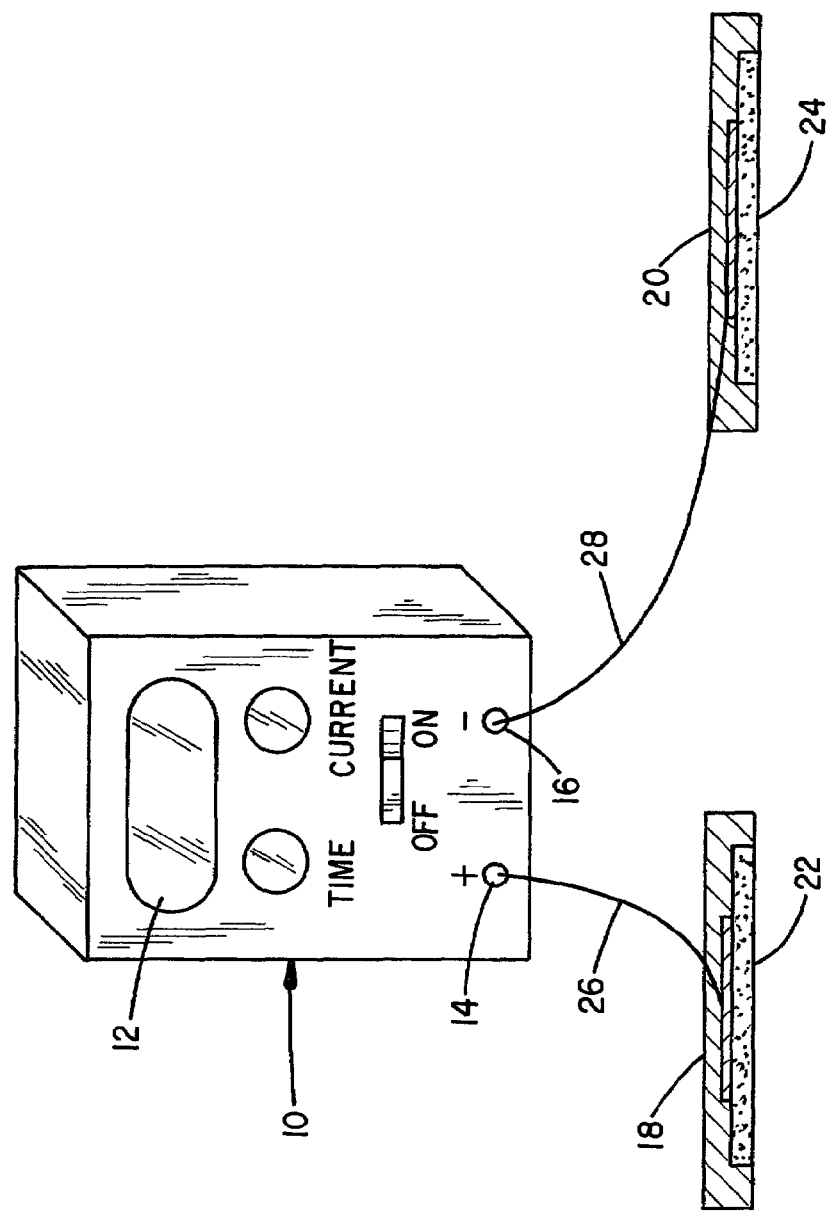
FIG. 1 is a schematic perspective diagram of a conventional externally-powered iontophoresis device utilizing a connected timer in DC current source.
Figure 2:
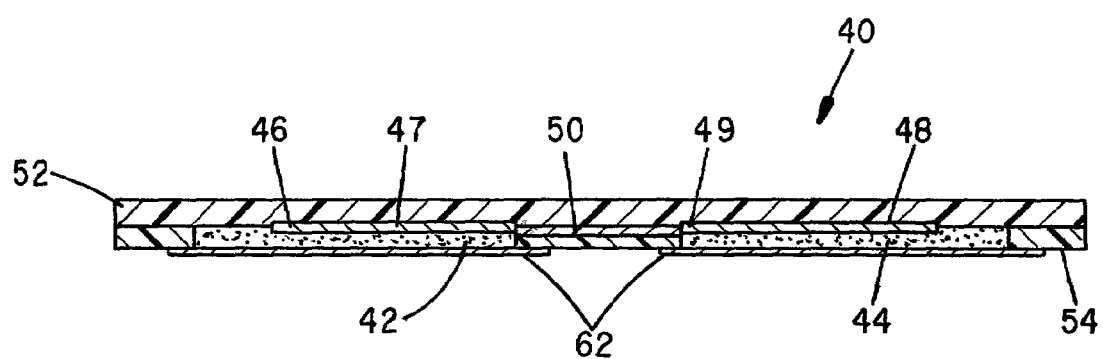
FIG. 2 depicts a cross-sectional schematic drawing of one embodiment of a wearable patch constructed in accordance with the invention.
Figure 3A:
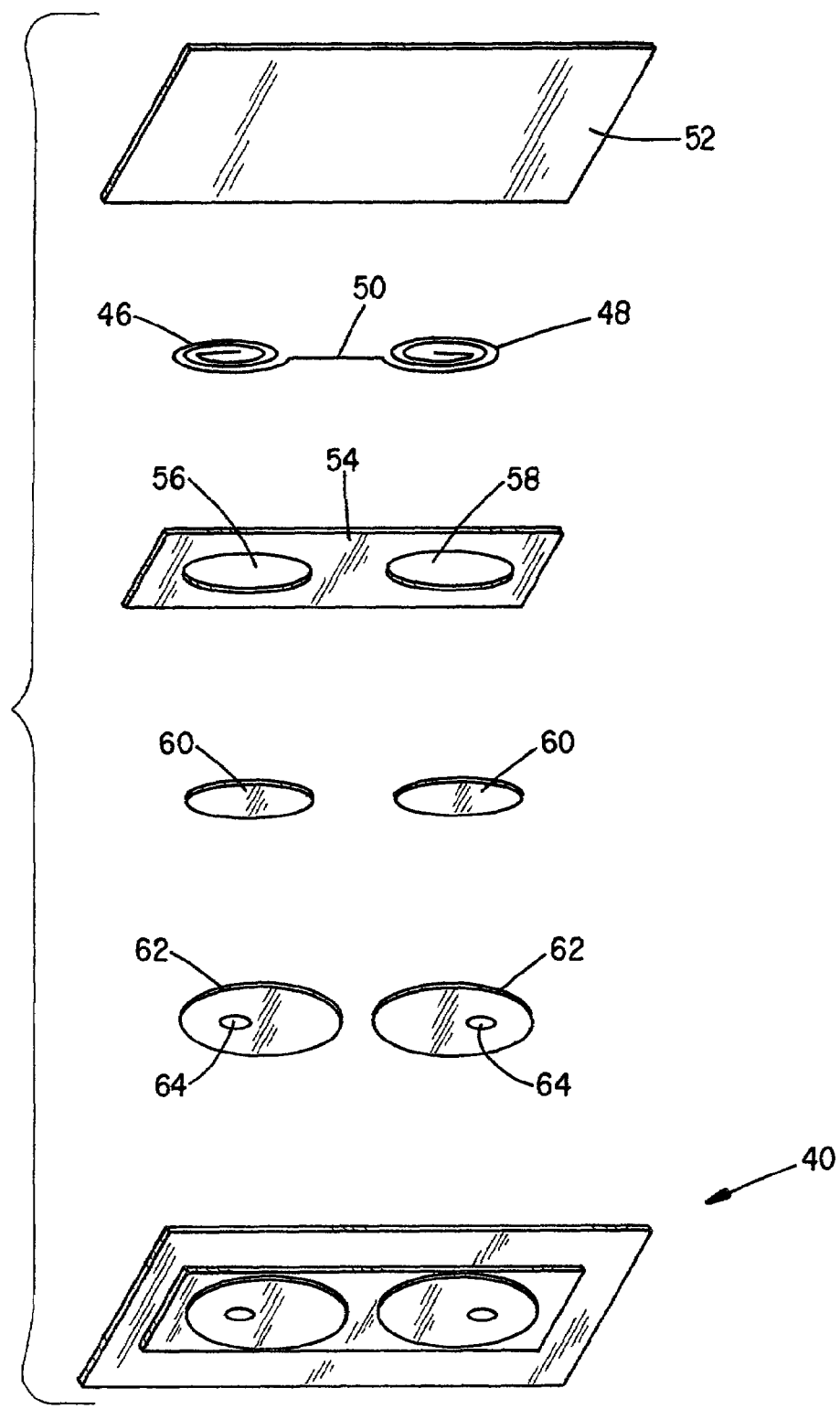
FIG. 3A is an exploded view showing the assembly of the wearable patch shown in FIG. 2.

As previously indicated, and as shown in FIGS. 2 and 3A, the iontophoretic wearable patch of the invention shown generally at 40 includes two chambers; namely, a cationic drug chamber 42 and an anionic drug chamber 44. For the purposes of this description, the cationic drug chamber may be described as one containing a return electrode 46 which comprises or otherwise is provided with an electrochemically oxidizable species, such as by a coating on the electrode at 47. The anionic drug chamber includes a working electrode 48 which is comprised of or otherwise contains an electrochemically reducible species, which also may be in the form of a coating at 49. The chambers are typically separated by a known distance which is optimally between about 0.1 cm and 2 cm, keeping in mind that other distances can be used, but that it is desirable to maintain the iontophoretic patches as rather small in size. The cationic chamber electrode 46 and the anionic chamber electrode 48 are electrically connected by a conductor at 50 which is typically a common wire (FIG. 3A).

Other components of the patch include an impervious non-conducting flexible backing layer 52 which can be constructed using 3M polyethylene tape #1523, or other occlusive material. Holding the electrodes in place and attached to the backing material is a cell wall defining layer 54 which has two separated openings 56 and 58 to define anode and cathode cell or chamber cavities. The cell wall defining layer can be constructed of 3M #1772 or similar material. A hydrophilic absorbent layer as at 60 is added to each of the cavities defined by the cell wall defining layer and serves to retain fluid in the cell cavity. The hydrophilic layer 60 can be a material which forms a hydrophilic gel when contacted with aqueous solution such as polyacrylamide or it can be cotton, gauze, or other hydrophilic material. A current distribution layer 62 associated with each cell cavity is one device that serves to hold the hydrophilic absorbent layer in place and is permeable to passage of drug molecules. Porous membrane materials such as nylon, polycarbonate, eva, and cellulose acetate are suitable for use as current distribution layer materials. Within the porous membrane is a circular opening or inlet port 64 of approximately 4 mm in diameter, which serves as an inlet port for drug containing fluids.

Figure 3B:
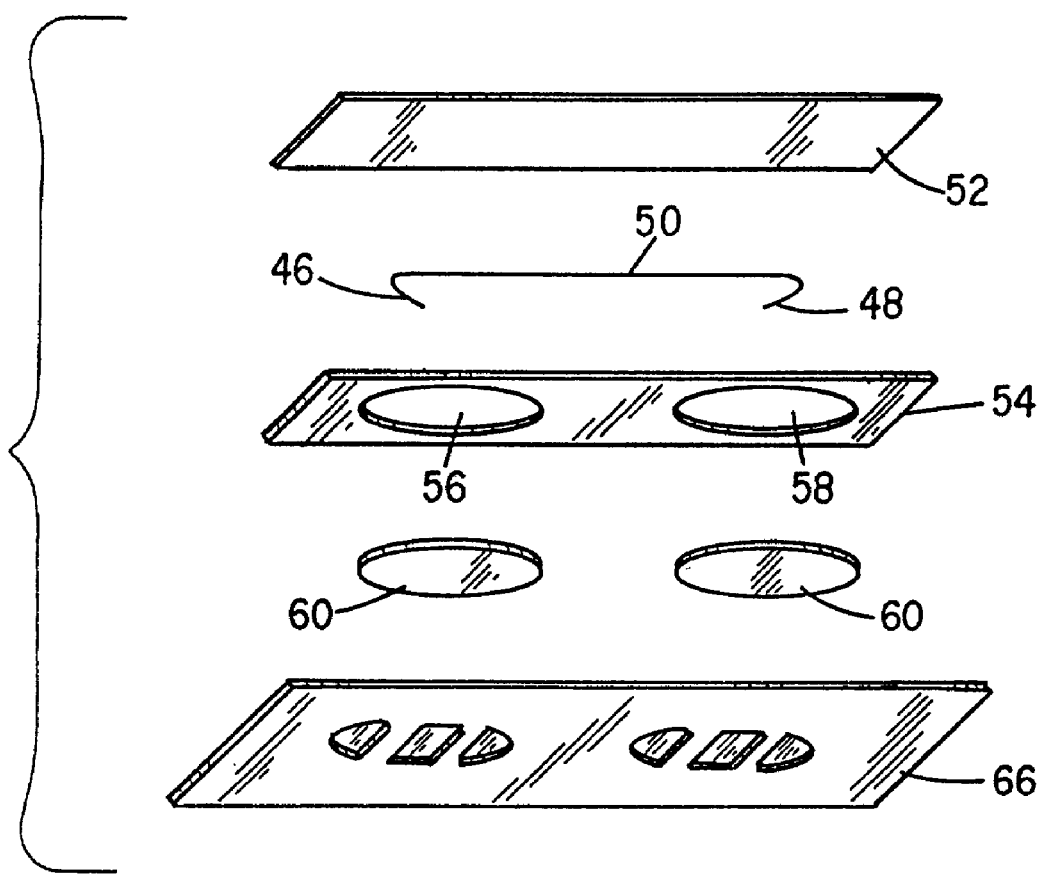
FIG. 3B is an exploded view showing the assembly of an alternative embodiment of the wearable patch of the invention.

In the embodiment of FIG. 3B, the current distribution layers 62 are replaced with a hypoallergenic adhesive layer 66 which is also drug permeable. This illustrates that the current distribution layer is optional and can be replaced when other means to secure the hydrophilic absorbent layer in place are provided. Depending on the nature and charge of the drug to be delivered, it may be placed in either the anodic or cathodic chamber.

The oxidizable species and the reducible species of the galvanic battery or couple are selected so as to provide a spontaneous galvanic potential when the iontophoretic patch is in contact with the body. Examples of suitable oxidizable species include zinc and magnesium. Examples of suitable reducible species include silver chloride and cupric oxide. When zinc is used as the oxidizable species and silver chloride is used as the reducible species, the galvanic potential established is approximately 1 volt. When magnesium is used as the oxidizable species and silver chloride is used as the reducible species, the galvanic potential established is approximately 2.6 volts.

During the iontophoretic process of this invention, as current flows, the oxidizable species in the cationic drug chamber becomes oxidized, while the reducible species in the anionic chamber becomes reduced. The galvanically induced current will continue to flow until depletion of either the oxidizable or reducible species, whichever is present in limiting amount. The relationship between the amount of current flow and the amount of oxidizable or reducible species in limiting supply, is theoretically represented by Faradays constant; one gram equivalent of the limiting reducible or oxidizable species will provide one Faraday (96,487 coulombs) of electricity.

At a given potential, the rate that medications are introduced is a function of the level of current while the total quantity of medication delivered is a function of both current level and the time, i.e., the amount of total charge transferred. Because of this relation, the quantity of medication introduced by iontophoresis is often referred to in units of mA-minutes of dosage. Thus, for example, an equivalent 40 mA-minute dosage can be delivered at different rates; 0.1 mA for 400 minutes, 1 mA for 40 minutes, 10 mA for 4 minutes, etc. Labeling, of course, can also be in units of charge (coulombs in addition to mA-minutes), equivalent amount of drug (mass, moles), time (hours), amount of electrode material (mass, moles), or other units that relate to total charge capacity of the galvanic couple power source or other battery that gets delivered.

The iontophoretic patch of this invention will optimally deliver a fixed and known charge between 0.06 and 60 coulombs, which corresponds to between 0.00000062 and 0.00062 gram equivalent weight of oxidizable or reducible species in limiting supply. Clearly, consistency at these low amounts is a challenge.

Preparation of the iontophoretic electrodes of this invention is critical, as a known limiting amount of electroactive species must be incorporated within, or onto, either the anode electrode, the cathode electrode, or both. In preparation of the cationic drug chamber electrode, oxidizable wire or foil material can be used of known weight and purity; or an oxidizable coating of known amount can be deposited on the surface of an electrically conductive substrate. For example, a known amount of molten zinc or magnesium can be deposited over a wire substrate to produce an electrode with known oxidizable species content. In preparation of the anionic drug chamber electrode, a reducible coating of known amount is deposited on the surface of an electrically conductive substrate. For example, a known amount of molten silver chloride can be deposited over a wire substrate to produce an electrode with known reducible species content. Alternatively, a known amount of silver chloride can be generated on the electrode surface by an electrolytic or electroplating process, such as by electrolytic oxidation of a silver wire in the presence of chloride, to produce a coating of silver chloride.

One approach to preparation of the iontophoretic electrodes of this invention is to dip one end of a silver wire into molten zinc or magnesium and electrolytically generate a known amount of silver chloride on the other end of the wire. This process yields a controlled dosage galvanic battery, which is assembled into the iontophoretic patch as shown in FIGS. 3A and 3B.

In accordance with, and as exemplified by, the above preparation techniques, all of the electroactive species of the electrodes have direct access to the common conductor or base connecting material. It is an important aspect of the invention that the physical connection and proximity between all of the electroactive species materials and base connector materials is such that all of said electroactive species available have conductive access thereto during the operation of the device. The ability to predict full consumption is critical.

As previously indicated, consumption of oxidative and reductive materials can occur in an unpredictable manner and prior art galvanic electrodes can fail prematurely owing to a break in electrical contact prior to full consumption of material. This can occur in some configurations because of uneven consumption of material. We have also discovered that when worn, skin patch delivery devices are subjected to mechanical stress with body movement. With many electrode designs, a portion of the electroactive species can become mechanically separated from the conductive connector, resulting in electrical isolation and premature suspension of delivery. This problem can be solved by disposing the oxidative and reducible materials so as to be fully consumed, e.g. by depositing them as very thin coatings ($\leq 0.5$ mm thick) over a continuous electrical connector.

It is well known in manufacturing piece parts that costs are reduced by production in high volume, typically large batch (or lot) quantities. However, it has been discovered that mass production of iontophoretic power supplies to deliver a fixed, pre-determined charge or dosage within close tolerances is difficult to accomplish. In producing large batch quantities, there inevitably exists variability associated with the manufacturing process. Thus, for example, the actual capacity of power supplies produced and so the associated dosage produced in a manufacturing lot often deviates from the capacity intended (or "target") dosages.

Additionally, it has been discovered that drift can occur during processing to cause a segment of a lot to deviate from the rest. For example, in building a sequence of parts which constitute a manufacturing lot, nominally between 1,000 and 1,000,000 parts, a first portion of the lot may deviate from a middle or end portion. Even when several devices are prepared in a single manufacturing step, deviations can occur between groupings.

As indicated, an important aspect of the present invention involves the manufacture of the galvanic power source couples or cells and half cells utilized in the iontophoresis patches and more, particularly, a method in which the cells of a lot or batch of cells are characterized in terms of actual manufactured capacity rather than simply a target capacity. As used herein, the terms "batch" or "lot" of cells or power sources is defined to be inclusive of all numbers of devices and manufacturing techniques including continuous production approaches. This enables, in turn, a sufficient capacity predictability in devices using such cells that the capacity of the resulting patches may be labeled with a high degree of confidence.

The power sources of the present invention may be fabricated by conventional means using paste-type materials in conjunction with well known screen printing and baking (drying) processes. While this enables generally accurate layer thicknesses to be produced, the results can vary somewhat from batch to batch and also across the area of the same batch. Thus, although the power sources may be intended to be built to a particular capacity, unless the capacity of the power sources or source components of the batch or lot is adequately tested, the actual capacity cannot be accurately predicted. Accordingly, it has been found that an adequate amount of testing is required to properly characterize the charge capacity a given process lot of cells or half-cells in order that the dosage of corresponding iontophoretic devices employing these components can be reliably designated or labeled.

The following tables represent examples of lots of representative sampling test results for lots or batches of galvanic couple cells or half cells tested to exhaustion. The sampling procedure used is meant to be representative, it being realized that other acceptable methods exist and could be used.

Testing has been done in accordance with American National Standard Sampling Procedures and Tables for Inspection by Variables for Percent Non-Conforming, prepared by American Society for Quality Control Standards Committee for American National Standards Committee Z-1 on Quality Assurance. This is an acceptable sampling procedure to be used on a continuing stream of lots for AQL specified. It provides tightened, normal and reduced plans to be used on measurements which are normally distributed. Variations may be measured by sample standard deviation, sample range or known standard deviation. The present revision is known as ASQ/ANSI Z1.9-1993 corresponds directly to the military standard MIL-STD-414. That spec is based on the following inputs:

Inspection Level-II
Normal Inspection AQL=1.5%
Variability Unknown
Double Spec Limit ($\pm 10\%$)

For lot sizes between 10,000 and 35,000, the sample size is n=100. For lot sizes between 35,001 and 150,000, the sample size will be n=150. For lot sizes between 150,001 and 500,000, the sample size will be n=200.

| Example I Lot Size 26,994 | |
| --- | --- |
| Sample Size | 100 |
| Average | 77.65 |
| Standard Deviation | 2.49 |
| Estimated Percent Nonconforming Above Upper Limit | 0 |
| Estimated Percent Nonconforming Below Lower Limit | 1.087 |
| Estimated Total Percent Nonconforming | 1.087 |
| Maximum Allowable Percent Nonconforming | 3.06 |
| Meet Specification? Yes or No | — |
| Will Trimming Reduce Percent nonconforming? Yes or No | NA |

| Example II Lot Size 70,000 | |
| --- | --- |
| Sample Size | 150 |
| Average | 79 |
| Standard Deviation | 3.5 |
| Estimated Percent Nonconforming Above Upper Limit | 0.473 |
| Estimated Percent Nonconforming Below Lower Limit | 2.22 |
| Estimated Total Percent Nonconforming | 2.69 |
| Maximum Allowable Percent Nonconforming | 2.88 |
| Meet Specification? Yes or No | — |
| Will Trimming Reduce Percent nonconforming? Yes or No | |

| Example III Lot Size 187,640 | |
| --- | --- |
| Sample Size | 200 |
| Average | 78.9 |
| Standard Deviation | 3.5 |
| Estimated Percent Nonconforming Above Upper Limit | 0.441 |
| Estimated Percent Nonconforming Below Lower Limit | 2.40 |
| Estimated Total Percent Nonconforming | 2.841 |
| Maximum Allowable Percent Nonconforming | 2.86 |
| Meet Specification? Yes or No | — |
| Will Trimming Reduce Percent nonconforming? Yes or No | NA |

To use the controlled dosage iontophoresing device, solution containing cation to be delivered is injected into the inlet port of the cationic drug chamber and solution containing anion material is injected into the inlet port of the anionic drug chamber. The patch is then applied to the portion of the body where drug is to be administered and adhered to the skin by an adhesive layer on the bottom of the patch and/or by an overlaying bandage material. Once contacted with skin, an electrical circuit is completed which allows passage of current and delivery of drug compounds.

Figure 4:
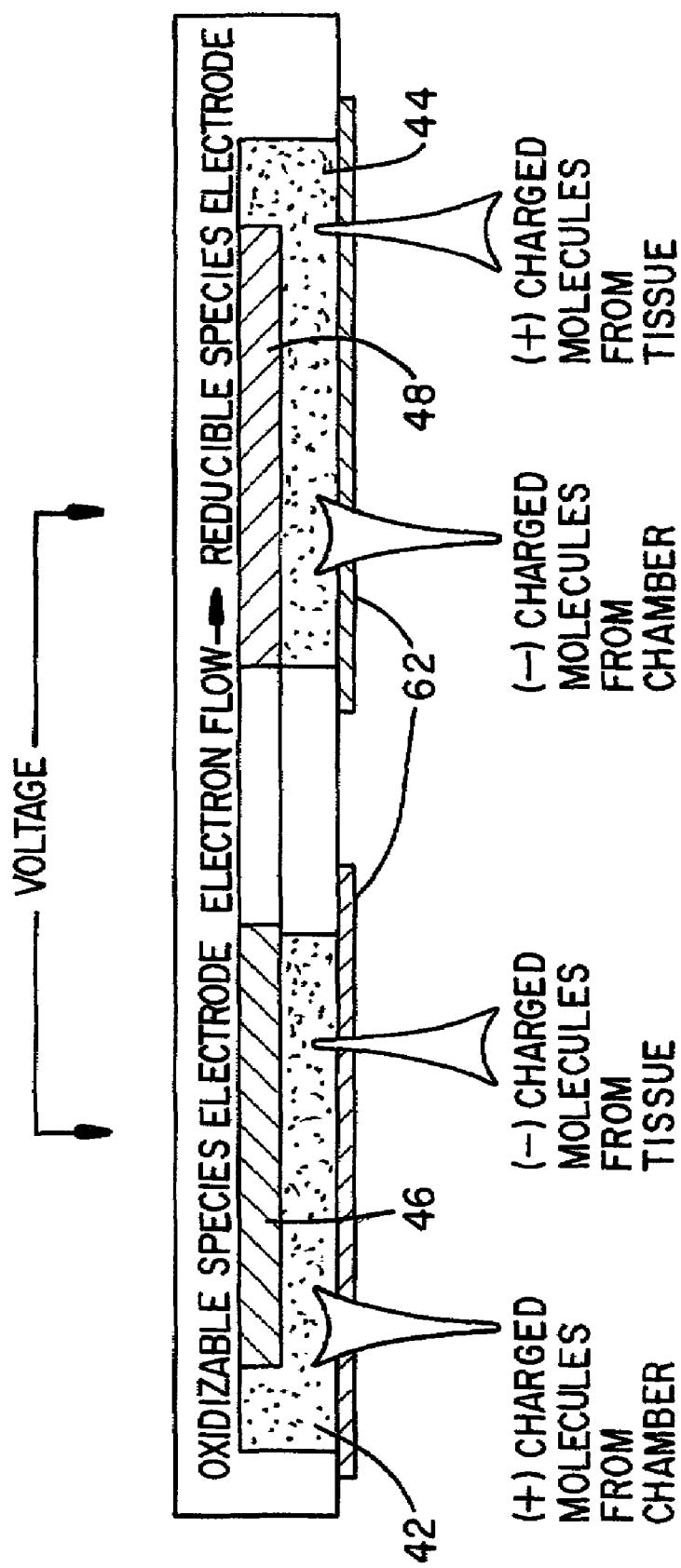
FIG. 4 is a schematic diagram illustrating the flow of molecules and electrons in accordance with the electro motive aspects of the wearable patch of the invention.
Figure 5:
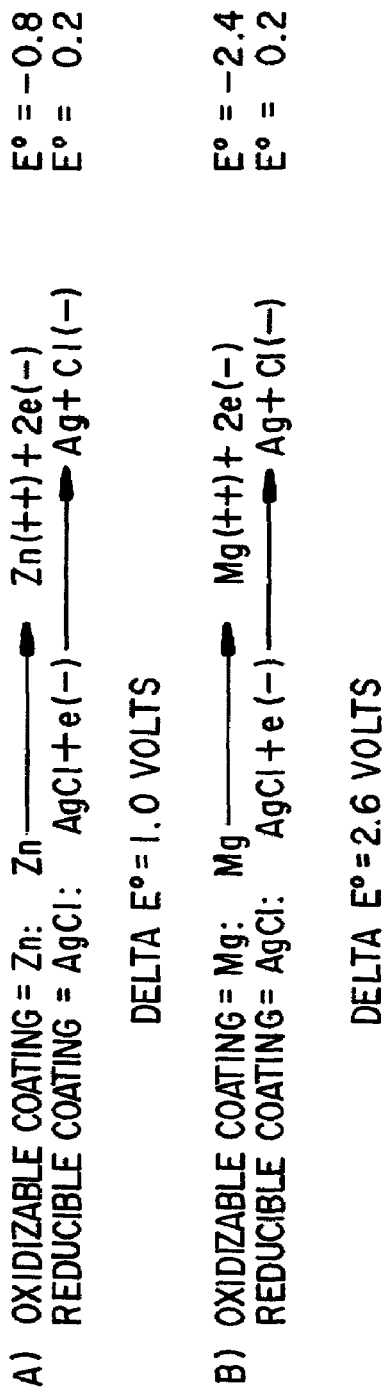
FIG. 5 illustrates examples of galvanic electrode reactions in accordance with the principles of the present invention.

FIG. 4 schematically illustrates the flow of electrons and ions during use of this invention. FIG. 5 shows electrochemical half reactions which can serve as means to provide stimulation current in this invention. When either the oxidizable material of the cationic chamber electrode is depleted, or the reducible material of the anionic drug chamber electrode is depleted, current flow falls to essentially zero and the delivery of drug compound is completed.

Figure 6:
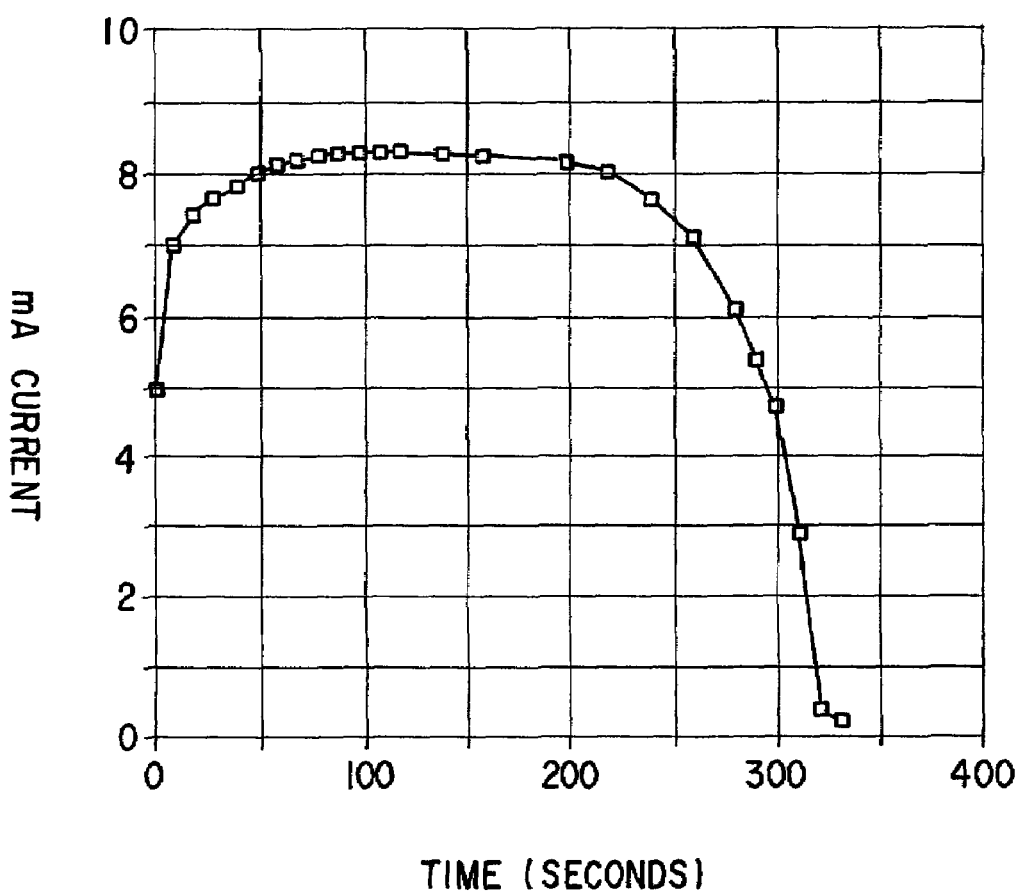
FIG. 6 is a plot of current flow versus time showing the galvanic limiting affect of reducible agent depletion.

FIG. 6 illustrates the fixed delivery of current as a function of time from a battery prepared in accordance to this invention. In this experiment, a zinc wire serves as the oxidizable species and the reducible species was a limiting supply of electroplated silver chloride deposited over a silver wire. The zinc and silver chloride ends were placed in a 1% sodium chloride solution and current flow was measured by an ammeter in direct connection. The current measured was steady, then depleted rapidly to near zero after approximately 5 minutes of use.

Figure 7:
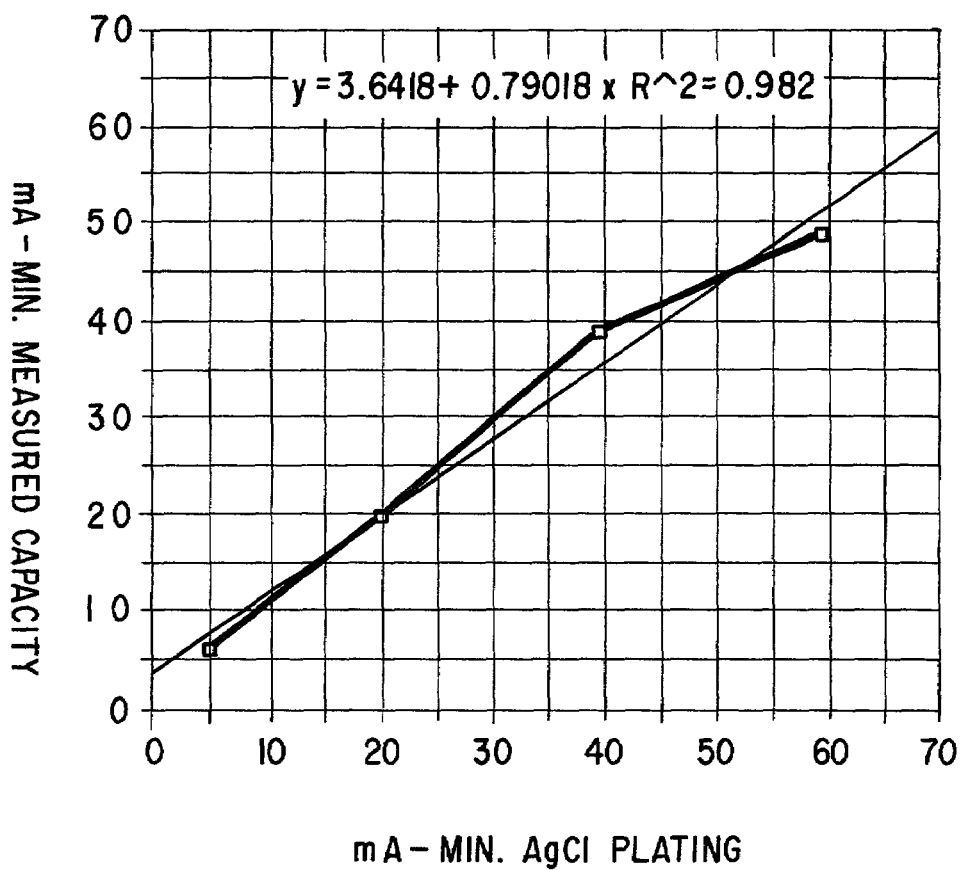
FIG. 7 graphically depicts the generally linear relationship between the limiting supply of electroplated reducible species (anode limiting) and the capacity of the galvanic battery of the invention.

In FIG. 7, results from similar experiments using varying amounts of limiting silver chloride is shown. This illustrates how a limiting supply of the reducible species, silver chloride, can be used to establish and control the battery capacity in the iontophoretic patch of this invention.

Figure 8:
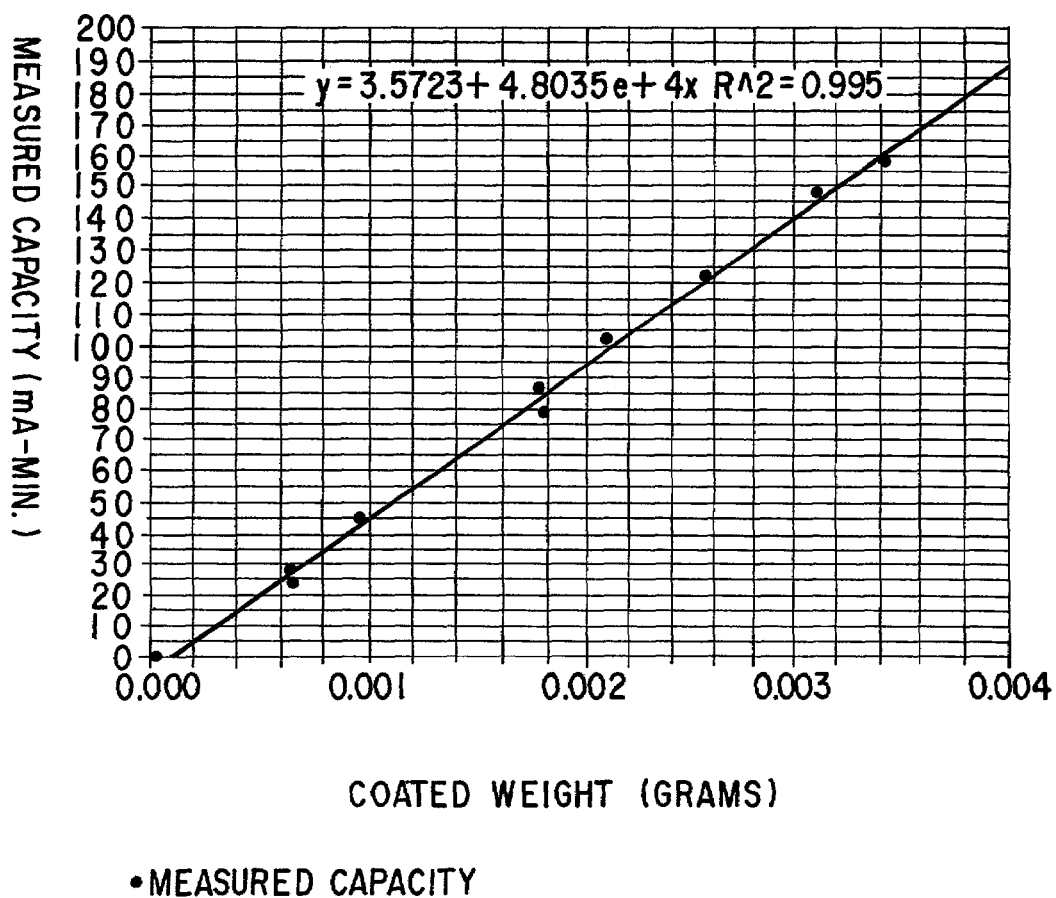
FIG. 8 graphically depicts the generally linear relationship between the limiting supply of oxidizable zinc coating (cathode limiting) and measured galvanic battery capacity in accordance with the invention.

FIG. 8 illustrates results similar to that shown in FIG. 7 using varying limiting amounts of the oxidizable material, zinc, rather than the reducible species, silver chloride. The figure illustrates how a limiting supply of oxidizable material can be used to establish and control the battery capacity in the iontophoretic patch of the invention in the same manner as the reducible material.

Figure 9:
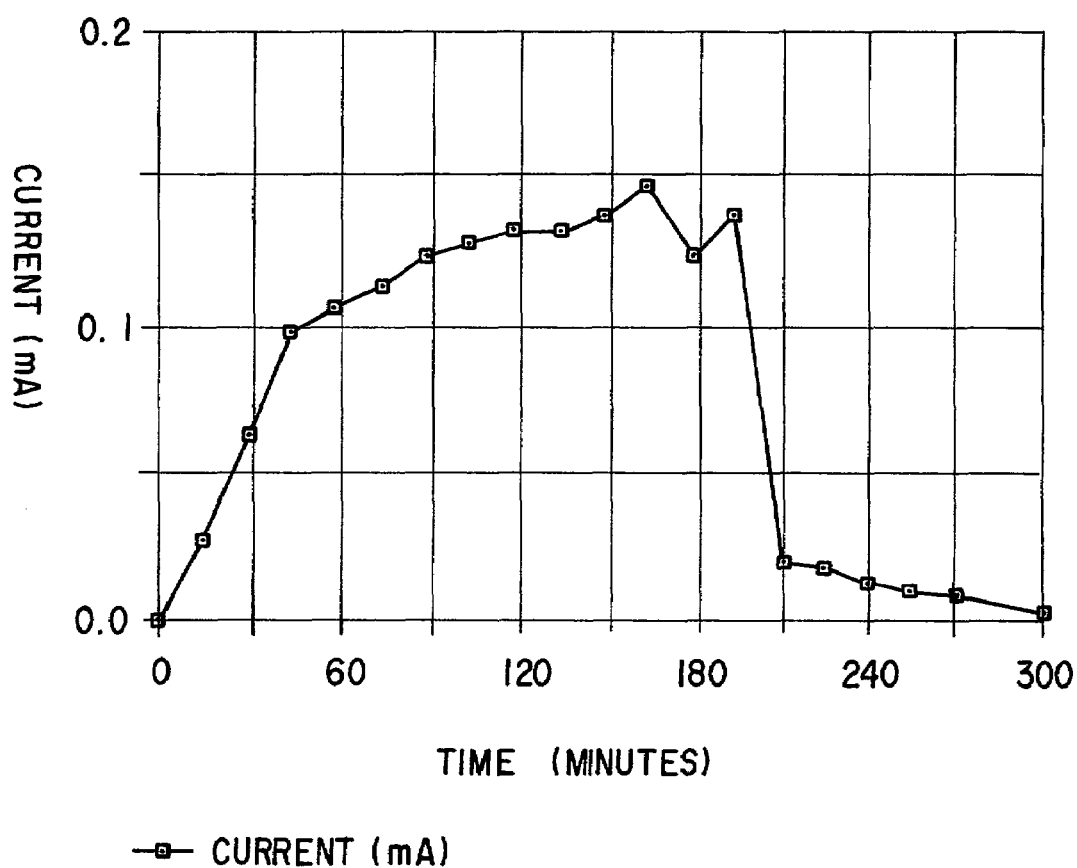
FIG. 9 graphically depicts experimental results showing current flow v. time for a patch made in accordance with the invention as applied to human skin, also depicting the depletion time.

FIG. 9 is an illustration of current flow from a patch produced in accordance with the present invention when applied on human skin using a 1% sodium chloride solution in both chambers. In the experiment which produced the results of FIG. 9, zinc of a known quantity was deposited in a limiting amount as the oxidizable species, with silver chloride deposited in excess amount as the reducing species making this battery or cell cathode limited. In this example, current flow reached approximately 0.1 mA and held relatively steady until the zinc became depleted at about 190 minutes. Thereafter, the current rapidly dropped to near 0.

While the power sources are galvanic cells in accordance with invention thus may be made capacity limited based on the oxidizable or based on the reducible material in the galvanic couple, an additional advantage may be achieved by making the controlling or limiting amount the oxidizable species. When this is done and the conductor connecting the oxidizable species with the reducible species corresponds to the reduction product of the reducible species, upon depletion of the oxidizable species, there results a net zero potential difference state between the half-cells. This prevents further reduction of oxygen in the system which may otherwise be experienced and which results in a characteristic and undesirable change in the pH of the drug chamber of the device along with the production of current and beyond the desired dosage limit of the skin patch or other such device involved. Thus, for example, in a Zn/AgCl system, preferably the Zinc and silver chloride should be connected by, or even deposited on a connecting silver conductor such as when the Zinc is depleted in the cell, such a net zero potential, non-reactive state is achieved.

Figure 10:
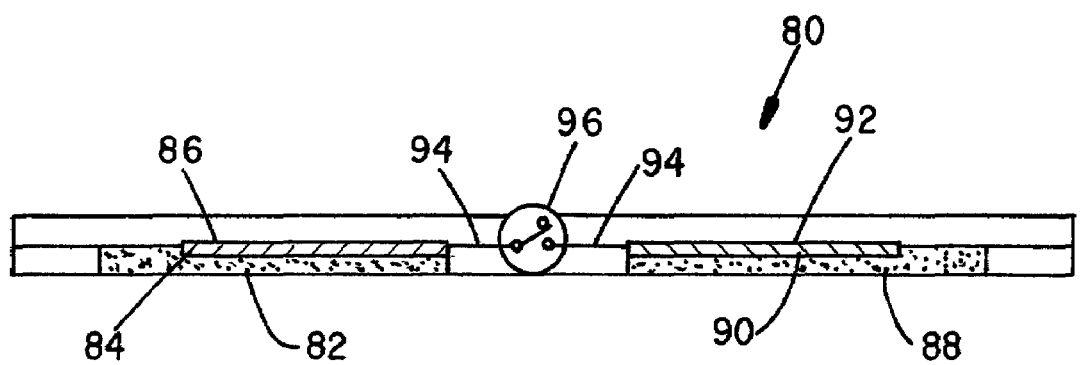
FIG. 10 is a cross-sectional schematic drawing of an alternate embodiment of a wearable patch constructed in accordance with the invention.

In addition to the embodiments described above, additional features such as the utilization of an ON/OFF switch which would allow the patient to interrupt current flow voluntarily may be added to the patch system. Such an embodiment is depicted generally at 80 in FIG. 10. That system includes cathodic drug chamber 82 containing a return electrode 84 having an oxidizable electrode coating 86 and an anodic drug chamber 88 containing a working electrode 90 with a reducible electrode coating 92. In this embodiment electrical connecting element 94 that connects the working and return electrodes is provided with a manually operable switch or disconnect device 96 which can be opened to interrupt the galvanic current as shown in the Figure. With the switch 96 closed, of course, the system operates as shown in the embodiment of FIG. 2. This feature provides an optimal additional level of control to the patient with regard to the administration of a therapeutic agent.

This invention has been described herein in considerable detail in order to comply with the patent statutes and to provide those skilled in the art with the information needed to apply the novel principles and to construct and use such specialized components as are required. However, it is to be understood that the invention can be carried out by specifically different devices, and that various modifications, both as to the equipment details and operating procedures, can be accomplished without departing from the scope of the invention itself.

For example, those skilled in the art will recognize that many variations of materials and shapes of wire substrates are possible in creating the galvanic couple or battery for use in the wearable patch of the invention. In addition to silver wire, in some cases virtually any electrically conductive material can be used. These include, for example, copper wire, aluminum wire and/or any type of a printed circuit conductor provided on a non-conducting substrate. In addition, the techniques for applying both the oxidizable and reducible constituents of the galvanic couple or battery to the conducting substrate are many and others such as microdispensing, adhesive coating, screen printing, sputtering or the like will also occur to those skilled in the art and any workable process in which the amount of applied material can be regulated are contemplated by this inven-

What is claimed is:

1. A method of providing reliable dosage ratings for the administration of therapeutic agents in transdermal iontophoresis devices that include a reservoir for holding a therapeudic agent comprising steps of:
   (a) providing a commonly manufactured lot of galvanic battery power sources each power source including
      (i) an oxidizable species and a reducible species wherein said self-contained galvanic power source provides the sole source of both the power and control for dosage delivery and contains a lesser amount of a selected one of said oxidizable species and reducible species;
      (ii) a common conductor for carrying said oxidizable species and said reducible species;
   (b) determining by sample testing in accordance with lot size characteristics of said lot including an average charge capacity for said galvanic battery power sources of said lot to produce a tested lot;
   (c) incorporating a galvanic power source from said tested lot into each said device;
   (d) labeling a delivery dosage rating for said devices as verified by said average charge capacity of said tested lot.

2. A method as in claim 1 wherein said iontophoresis devices are wearable skin patches.

3. A method as in claim 2 further comprising the step of packaging said iontophoresis devices independent of a therapeutic agent to be administered.

4. A method as in claim 1 further comprising the step of packaging said iontophoresis devices independent of a therapeutic agent to be administered.

5. A method as in claim 1 including the further step of providing a circuit-interrupting switch in series with said galvanic power source in said iontophoresis devices.

6. A method as in claim 1 wherein said galvanic battery power sources have an average charge capacity $\leqq 60$ coulombs.

7. A method of providing reliable dosage ratings for the administration of therapeutic agents in transdermal wearable skin patch iontophoresis devices that include a reservoir for holding a therapeudic agent comprising steps of:
   (a) providing a commonly manufactured, relatively large lot of galvanic battery power sources each power source including
      (i) an oxidizable species and a reducible species wherein said galvanic power source provides the sole source of both the power and control for dosage delivery and contains a lesser amount of said oxidizable species than said reducible species;
      (ii) a common conductor for carrying said oxidizable species and said reducible species which are disposed in relation to said conductor so as to be fully consumed, said common conductor corresponding to the reduction product of said reducible species;
   (b) determining by sample testing in accordance with lot size characteristics of said lot including an average charge capacity for said galvanic battery power sources of said lot to produce a tested lot;
   (c) incorporating a galvanic power source from said tested lot into each said device;
   (d) labeling said transdermal iontophoresis device with a delivery dosage rating for said devices as verified by said average charge capacity of said tested lot.

8. A method as in claim 7 further comprising the step of packaging said iontophoresis devices independent of a therapeutic agent to be administered.

9. A method as in claim 7 including the further step of providing a circuit-interrupting switch in series with said galvanic power source in said iontophoresis devices.

10. A method as in claim 7 comprising the further steps of applying said common conductor as a coating on a nonconductive substrate and applying said oxidizable and said reducible species as coatings on said common conductor.

11. A method as in claim 10 wherein said coatings are applied using screen printing techniques.

12. A method as in claim 7 wherein each said lot of commonly manufactured galvanic battery power sources includes at least 10,000 such sources.

13. A method as in claim 12 wherein said galvanic battery power sources have an average charge capacity $\leqq 60$ coulombs.

14. A method of providing a dosage rating for a transdermal iontophoresis therapeutic agent delivery device having a self-contained combined power source a reservoir for holding a therapeudic agent and dosage control system including a galvanic couple source, having electroactive materials disposed so as to be fully consumed, selected from a commonly manufactured relatively large lot of such sources, including the step of sampling and testing average charge capacity of a lot from which said galvanic power source is taken in accordance with lot size and using test results to produce said rating and providing said transdermal iontophoresis with said rating.

15. A transdermal iontophoretic therapeutic agent delivery device comprising:
   (a) a power source and control system further comprising a galvanic couple power source, wherein said galvanic couple power source alone provides the power for the device and the control for both dosage rate and dosage amount of therapeutic agent delivered;
   (b) wherein said galvanic couple power source is selected from a manufactured lot of galvanic couples of tested average charge capacity; and
   (c) a label associated with said delivery device identifying the charge capacity of said delivery system based on average tested charge capacities of a corresponding commonly manufactured lot of galvanic couple power sources from which it was obtained a reservoir for holding a therapeutic agent.

16. A delivery device as in claim 15 wherein said galvanic couple power source further comprises:
   (d) an oxidizable species in contact with a first delivery chamber for a therapeutic agent;
   (e) a reducible species in contact with a second delivery chamber for a therapeutic agent, said reducible species being supplied in a greater amount than said oxidizable species such that said oxidizable species is first depleted; and
   (f) a common electrically conductive substrate carrying said oxidizable and said reducible species which are disposed in relation to said conductor so as to be fully consumable and allowing the passage of a galvanic electric current therebetween, wherein said common conductor corresponds to the reduction product of said reducible species.

17. A delivery device as in claim 16 further comprising switch for interrupting the passage of said galvanic current.

18. A delivery device as in claim 16 wherein each said delivery chamber is provided with an amount of a hydrophilic absorbent material for retaining fluid in the chamber cavity.

19. A delivery device m as in claim 16 wherein each said delivery chamber is provided with an inlet port for admitting drug containing fluids.

20. A delivery device as in claim 16 wherein said common electrically conductive substrate is a coating on a nonconductive substrate.

21. A delivery device as in claim 20 wherein said oxidizable and said reducible species are coatings produced by screen printing.

22. A delivery device as in claim 21 wherein said common electrically conductive substrate coating is produced by screen printing.

23. A delivery device as in claim 16 wherein said oxidizable and said reducible species are coatings on said common electrically conductive substrate.

24. A delivery device as in claim 23 wherein said electrically conductive substrate is a wire.

25. A delivery device as in claim 23 further comprising a current distribution layer permeable to the passage of drug molecules overlaying the hydrophilic absorbent material and holding it in place.

26. A delivery device as in claim 23 wherein said oxidizable and said reducible species are coatings produced by screen printing.

27. A delivery device as in claim 23 wherein said common electrically conductive substrate is a coating on a non-conductive, substrate.

28. A delivery device as in claim 16 wherein said oxidizable species is selected from Mg and Zn and said reducible species is AgCl.

29. A delivery device as in claim 28 wherein said electrically conductive substrate is a silver wire.

30. A delivery device as in claim 15 wherein each said delivery chamber is provided with an amount of a hydrophilic absorbent material for retaining fluid in the chamber cavity.

31. A delivery device as in claim 30 wherein said hydrophilic absorbent material is selected from cotton, gauze and hydrophilic gels.

32. A delivery device as in claim 30 further comprising a current distribution layer permeable to the passage of drug molecules overlaying the hydrophilic absorbent material and holding it in place.

33. A delivery device as in claim 15 wherein each said delivery chamber is provided with an inlet port for admitting drug containing fluids.

34. A delivery device as in claim 30 further comprising an adhesive layer for adhering said delivery system to the skin of a patient and retaining said hydrophilic material in said chambers.

35. A delivery device as in claim 15 further comprising switch for interrupting the passage of said galvanic current.

36. A method as in claim 15 wherein said galvanic battery power sources have an average charge capacity $\leq$ 60 coulombs.

* * * * *

UNITED STATES PATENT AND TRADEMARK OFFICE
CERTIFICATE OF CORRECTION

PATENT NO. : 7,031,768 B2  
APPLICATION NO. : 10/166157  
DATED : April 18, 2006  
INVENTOR(S) : Carter R. Anderson Page 1 of 1

It is certified that error appears in the above-identified patent and that said Letters Patent is hereby corrected as shown below:

On the front page of the patent, in column 1, under Related U.S. Application Data, box (63), please replace the sentence:

"Continuation-in-part of application No. 09/674,211, filed on Dec. 18, 2000, now abandoned."

with

--Continuation-in-part of application No. 09/674,211, filed on Dec. 18, 2000, now abandoned, which is a National Stage Entry of PCT/US99/18861, filed on Aug. 18, 1999.--

Signed and Sealed this  
Twenty-sixth Day of June, 2012

David J. Kappos  
*Director of the United States Patent and Trademark Office*